United States Patent [19]
Iguchi et al.

[11] Patent Number: 5,612,158
[45] Date of Patent: Mar. 18, 1997

[54] ELECTROPHOTOGRAPHIC PHOTOCONDUCTOR AND PROCESS FOR PRODUCING THE SAME

[75] Inventors: Yasushi Iguchi; Sumitaka Nogami; Kyoko Kitagawa, all of Kawasaki, Japan

[73] Assignee: Fuji Electric Co., Ltd., Kawasaki, Japan

[21] Appl. No.: 625,214

[22] Filed: Apr. 1, 1996

[30] Foreign Application Priority Data

Mar. 31, 1995 [JP] Japan ................................. 7-074989

[51] Int. Cl.⁶ ............................................... G03G 5/14
[52] U.S. Cl. .............................. 430/58; 430/63; 430/65; 430/131
[58] Field of Search ........................... 430/58, 63, 65, 430/131

[56] References Cited

U.S. PATENT DOCUMENTS

| | | | |
|---|---|---|---|
| 5,391,448 | 2/1995 | Katayama et al. | 430/65 |
| 5,432,034 | 7/1995 | Nogami et al. | 430/58 |
| 5,489,496 | 2/1996 | Katayama et al. | 430/65 |

FOREIGN PATENT DOCUMENTS

| | | | |
|---|---|---|---|
| 576957 | 1/1994 | European Pat. Off. | |
| 48-47344 | 7/1973 | Japan. | |
| 52-25638 | 2/1977 | Japan. | |
| 57-81269A | 5/1982 | Japan. | |
| 58-95351 | 6/1983 | Japan. | |
| 62-280864 | 5/1987 | Japan. | |
| 2-181158 | 7/1990 | Japan. | |
| 4-172362 | 6/1992 | Japan | 430/63 |
| 6-202366A | 7/1994 | Japan. | |
| 6-186767 | 7/1994 | Japan | 430/131 |

*Primary Examiner*—Roland Martin
*Attorney, Agent, or Firm*—Spencer & Frank

[57] ABSTRACT

An electrophotographic photoconductor include an conductive substrate; an undercoat layer provided on the conductive substrate; and a photosensitive layer having charge-generation and charge-transport functions provided on the undercoat layer. The undercoat layer includes a polyamide resin and methylhydrogenpolysiloxane-treated titanium dioxide and preferably styrene-maleic acid half-ester copolymer. The photoconductor can be produced by the steps of: dispersing a polyamide resin and methylhydrogenpolysiloxane-treated titanium dioxide and preferably styrene-maleic acid half-ester copolymer in a mixture solvent of an alcohol-type solvent and a halogenated hydrocarbon-type solvent, thereby preparing a coating liquid for an undercoat layer; applying the coating liquid onto a conductive substrate, thereby providing an undercoat layer on the substrate; and forming a photosensitive layer on the undercoat layer.

10 Claims, 1 Drawing Sheet

ELECTROPHOTOGRAPHIC PHOTOCONDUCTOR AND PROCESS FOR PRODUCING THE SAME

BACKGROUND OF THE INVENTION

1. Field of the Invention

The present invention relates to an electrophotographic photoconductor and a method for producing the same. In particular, the present invention relates to an electrophotographic photoconductor comprising an undercoat layer provided between a conductive substrate and a photosensitive layer and a method for producing the same.

2. Description of the Prior Art

In general, the electrophotographic process using a photoconductive member has been used as one of the information recording means utilizing the photoconductive phenomenon caused by the photoconductive member. In this process, an image is formed in the following manner. That is, the photoconductive member is placed in the dark and charged of its surface by means of corona discharging, and the photoconductive member is exposed with light so that the charges on the exposed area are erased selectively. Thus, a latent electrostatic image corresponding to the unexposed area is formed. Subsequently, colored, charged fine particles (toner) are deposited on the latent electrostatic image by means of electrostatic attractive force or the like. Thus, the latent image is developed to form a visible image. In such electrophotographic techniques, the photoconductor used is required to have the following basic characteristics:

(1) it can be charged uniformly at an appropriate potential in the dark;

(2) it can have a high charge-retentivity or the charges present thereon are hardly discharged in the dark;

(3) it has an excellent photosensitivity and, therefore, can erase the charges thereon rapidly;

(4) the surface of the photoconductor can be discharged by light irradiation readily;

(5) it exhibits less residual potential;

(6) it has good mechanical strength and flexibility;

(7) it is stable in various electrical characteristics, particularly charging property, photosensitivity and residual potential under repeated use; and (8) it has a resistance against heat, light, temperature, humidity, deterioration with ozone and the like so that it has good stability and durability.

On the other hand, in the electrophotographic photoconductor currently used (which comprises a conductive substrate and a photosensitive layer provided on the conductive substrate), an undercoat layer has been provided between the substrate and the photosensitive layer for the purpose of satisfying the following requirements.

(1) To prevent the injection of unnecessary charges from the substrate into the photosensitive layer, so as to prevent the decrease in the surface potential of the photosensitive layer or prevent the generation of image defects during developing;

(2) To cover any defects present on the surface of the conductive substrate;

(3) To improve a charging property of the photoconductor;

(4) To improve an adhesion property of the photosensitive layer; and (5) To improve a coating property of the photosensitive layer to the conductive substrate.

The resin conventionally used for the undercoat layer is, for example, a resin material such as polyethylene, polypropylene, polystyrene, acrylic resin, vinyl chloride resin, vinyl acetate resin, polyurethane resin, epoxy resin, polyester resin, melamine resin, silicone resin, polybutyral resin, polyamide resin, etc. or a copolymer resin comprising at least two repeating unit members thereof such as vinyl chloride-vinyl acetate copolymer resin, acrylonitrile-styrene copolymer resin, etc. In addition, also used is casein, gelatin, poly(vinyl alcohol), ethyl cellulose, or the like. Among them, especially preferred is polyamide resin. (See Japanese Patent Application Laying-open Nos. 47344/1973, 25638/1977 and 95351/1983.)

However, in the above-mentioned electrophotographic photoconductors using a polyamide resin as the undercoat layer component, since the volume resistivity of the undercoat layer generally lies within the range from about $10^{12}$ to about $10^{15}$ ohm·cm, the undercoat layer should have a thickness as small as about 0.3 μm or less. In such case, if the thickness of the undercoat layer is thicker than about 0.3 μm, the residual potential is likely to be accumulated in the photoconductor, resulting in the occurrence of fogging on the copied image. On the contrary, if trying to make the thickness of the undercoat layer thinner, it tends to become difficult to control the thickness of the undercoat layer during coating, which may lead to the difficulty in sufficient covering of defects present on the conductive substrate with the undercoat layer, as well as the difficulty in the satisfactory improvement in charging property of the photoconductor obtained.

In these situations, some types of electrophotographic photoconductors have been proposed. For example, for the purpose of reducing the residual potential on the photoconductor and preventing the generation of defects of the image obtained, Japanese Patent Application Laying-open No. 280864/1987 discloses an electrophotographic photoconductor in which 1 to 10 parts by weight of a mixture of titanium oxide and tin oxide is dispersed in 100 parts by weight of nylon-8 resin to prepare an undercoat layer. Furthermore, for the purpose of improving the dispersibility of the titanium oxide in the resin component, Japanese Patent Application Laying-open No. 181158/1990 discloses an electrophotographic photoconductor in which alumina-coated titanium oxide particles are contained in the undercoat layer.

Thus, it has become possible to achieve the production of an electrophotographic photoconductor having a thick undercoat layer and having reduced residual potential by incorporating titanium oxide into the undercoat layer. However, in such photoconductor, a problem that the stability of the photoconductor under repeated use is affected by environmental conditions, particularly low-temperature/low-humidity conditions is still remaining.

For these reasons, there has been demanded an undercoat layer which can contribute to improving the charging characteristics and the residual potential, so that providing a photoconductor showing less accumulation of residual potential and less decrease in photosensitivity under repeated use and various environmental conditions. Accordingly, it is required for the resin material of the undercoat layer not to cause the aggregation of the charge-generation substance in the photosensitive layer when contacting with the photosensitive layer. It is because the aggregation of the charge-generation substance results in the non-uniform coating of the photosensitive layer onto the undercoat layer, which may cause the decrease in photosensitivity of the photoconductor and the non-uniformity in the contrast of image obtained. In addition, it is further required for the undercoat layer to have stable resistivity over wide environmental conditions including low-temperature/low-humidity and high temperature/high humidity conditions. Furthermore, it also be required for the undercoat layer to form a barrier against the injection of positive holes from the conductive substrate into the photosensitive layer and to have a resistance against solvents used for preparation of the photosensitive layer.

In the preparation of the coating liquid for the undercoat layer, an alcohol-type solvent such as methyl alcohol and ethyl alcohol has conventionally been used, since the main component of the undercoat layer is an alcohol-soluble nylon in most cases. However, the use of the solvent composed of alcohol-type solvent alone has a problem of non-uniformity in coating of the coating liquid onto the conductive substrate due to the non-uniform evaporation of the solvent after the coating. When the photosensitive layer contacts with the non-uniformly coated portion of the undercoat layer, the charge-generation substance in the photosensitive layer comes to cause aggregation at the portion, resulting in non-uniform coating of the photosensitive layer or the undercoat layer. These phenomena cause the decrease in photosensitivity of the photoconductor and the non-uniformity in the contrast of the copied image, which are disadvantageous.

SUMMARY OF THE INVENTION

In these situation, the present invention has been accomplished.

Accordingly, it is an object of the present invention to provide an electrophotographic photoconductor having excellent characteristics such as charging property and residual potential property and an excellent stability under repeated use and wide environmental conditions including low temperature/low humidity and high temperature/high humidity conditions.

Another object of the present invention is to provide a method for producing the above-mentioned electrophotographic photoconductor, by which the coating liquid for the undercoat layer can be applied onto the conductive substrate uniformly. This object can be achieved by improving the solvent used for the preparation of the undercoat layer.

According to one aspect of the present invention, there is provided an electrophotographic photoconductor comprising:

an conductive substrate;

an undercoat layer provided on the conductive substrate; and a photosensitive layer having both charge-generation and charge-transport functions provided on the undercoat layer, wherein said undercoat layer comprises a polyamide resin and a methylhydrogenpolysiloxane-treated titanium dioxide.

Here, the undercoat layer may further comprise styrene-maleic acid half-ester copolymer.

The polyamide resin may be nylon-12/6/66 copolymer.

The undercoat layer may have a thickness of within the range from 0.1 to 10 μm.

The photosensitive layer may have a functionally distinguishable laminate structure comprising a charge-generation layer having a charge-generation function and a charge-transport layer having a charge-transport function, in which the charge-generation layer and the charge-transport layer are laminated on the substrate in this order.

The photosensitive layer may have a single-layer structure.

According to another aspect of the present invention, there is provided a method for producing an electrophotographic photoconductor comprising the steps of:

(1) dispersing a polyamide resin and methylhydrogenpolysiloxane-treated titanium dioxide in a mixture solvent formed of an alcohol-type solvent and a halogenated hydrocarbon-type solvent, thereby preparing a coating liquid for an undercoat layer;

(2) applying said coating liquid onto a conductive substrate, thereby providing an undercoat layer on the substrate; and (3) forming a photosensitive layer on said undercoat layer.

Here, in the step (1), styrene-maleic acid half-ester copolymer may be further dispersed together with the polyamide resin and methylhydrogenpolysiloxane-treated titanium dioxide into the mixture solvent.

The step (3) may comprise the following steps of:

(a) forming a charge-generation layer on the undercoat layer; and (b) forming a charge-transpiring layer on the charge-generation layer.

The polyamide resin may be nylon-12/6/66 copolymer.

The above and other objects, effects, features and advantages of the present invention will become more apparent from the following description of embodiments thereof taken in conjunction with the accompanying drawings.

DETAILED DESCRIPTION OF THE PREFERRED EMBODIMENTS

The electrophotographic photoconductor according to the present invention comprises a conductive substrate, an undercoat layer provided on the conductive substrate and a photosensitive layer provided on the undercoat layer.

In the present invention, the material usable for the conductive substrate may be any substance which has been used for conventional conductive substrate. Examples of the material include metals such as aluminum, aluminum alloys, copper, zinc, stainless steel, nickel and titanium; laminates of polymeric materials such as poly(ethylene terephthalate), nylons and polystyrene or hard paper which are laminated with a metal foil such as aluminum; polymeric material or hard paper impregnated with conductive material which are deposited with aluminum, aluminum alloys, indium oxide, tin oxide or gold; and the like. With respect to the form or shape of the conductive substrate, there is not so particular limitation and any form of substrate may be used including those of drum, sheet, seamless belt, or the like.

In the present invention, the undercoat layer formed on the conductive substrate comprises a polyamide resin and methylhydrogenpolysiloxane-treated titanium dioxide. Particularly preferably, the undercoat layer further comprises a styrene-maleic acid half-ester copolymer together with the above two components. The addition of a styrene-maleic acid half-ester copolymer enables to improve the film forming property of the undercoat layer obtained, so as to improve the adhesion property of the undercoat layer to the conductive substrate.

The polyamide resin to be used in the present invention is not particularly limited and any one may be used as long as it can be used for the undercoat layer of an conventional electrosensitive layer. However, especially preferred polyamide resin is nylon-12/6/66 copolymer.

The nylon-12/6/66 copolymer can be prepared by copolymerizing lauric lactam and caprolactam with hexamethylenediamine adipate. In this copolymerization, these two components are used in amounts of equivalent relationship to one another. However, any nylon copolymer may be used in the present invention as long as it is soluble in alcohol and insoluble in any organic solvent used for preparation of a photosensitive layer. Specific nylon-12/6/66 copolymer preferably used in the present invention is a commercially available product "Daiamid" (a trade name by Daisel-Hüls).

The undercoat layer of the present invention further comprises methylhydrogenpolysiloxane-treated titanium dioxide together with the polyamide resin. In the present specification, the term "methylhydrogenpolysiloxane-treated titanium dioxide" (hereinafter, sometimes simply referred to as "treated titanium dioxide") means a high density dispersion of titanium dioxide particles in methylhydrogenpolysiloxane, in which the surface of each of the titanium dioxide particles is coated with methylhydrogenpolysiloxane. Accordingly, the use of the treated titanium dioxide in the undercoat layer enables to remarkably improve the dispersibility of titanium dioxide particles in the resin component of the undercoat layer.

Specific example of the treated titanium dioxide is a commercially available product "SI-UFTR-ZF" (a trade name by Miyoshi Kasei Inc.) in which ultra-fine particles of rutile-type titanium dioxide are dispersed in methylhydrogenpolysiloxane by a known method.

In the undercoat layer of the present invention, it is preferable to use the treated titanium dioxide in an amount of within the range of 50 to 70 wt % based on the total amount of the undercoat layer composition.

In the present invention, it is preferable that the undercoat layer further comprise styrene-maleic acid half-ester copolymer together with the polyamide resin and the treated titanium dioxide.

The styrene-maleic acid half-ester copolymer to be used in the present invention is also not so particularly limited as long as it is soluble in alcohol and insoluble in any of the organic solvent used for preparation of a photosensitive layer. Specific example of such styrene-maleic acid half-ester copolymer includes a commercially available product "Sprapal AP-20" (a trade name from BASF).

In the present invention, the styrene-maleic acid half-ester copolymer is mixed with the nylon-12/6/66 copolymer in an amount of 1 to 30 wt % based on the weight of the nylon-12/6/66 copolymer. The amount of the styrene-maleic acid half-ester copolymer not fall within the defined range is unfavorable in view of the film forming property of the resulting coating liquid for the undercoat layer.

The undercoat layer of the present invention can be formed by first dispersing the treated titanium dioxide and the polyamide and preferably the styrene-maleic acid half-ester copolymer in an organic solvent to prepare a coating liquid for the undercoat layer, and then applying the coating liquid onto a conductive substrate.

The organic solvent to be used for the coating liquid is a mixture solvent of an alcohol-type solvent, such as methanol or ethanol, and a halogenated hydrocarbon-type solvent, such as methylene chloride, dichloroethane or trichloroethane. As mentioned previously, if a solvent comprising an alcohol-type solvent alone is used as the solvent for the dispersion of the undercoat layer components, the aggregation of the undercoat layer components is likely to occur with the elapse of time during the preparation of the undercoat layer. As a result, the undercoat layer comes to have a non-uniform thickness. In the present invention, since a halogenated hydrocarbon-type solvent is additionally used in the solvent for dispersing the undercoat layer components, the stability in solubility of the undercoat layer components can be improved. As a result, the generation of the aggregates is reduced, so that the uniform coating of the undercoat layer onto the conductive substrate can be achieved.

In the present invention, it is preferred that the undercoat layer have a thickness of 0.1 to 10 μm and most preferably 0.2 to 1 μm. As mentioned above, if the thickness of the undercoat layer is more than 10 μm, undesirable residual potential is likely to be accumulated in the photoconductor, resulting in the occurrence of fogging on a copied image. On the other hand, if the thickness of the undercoat layer is less than 0.1 μm, the undercoat layer is likely to be non-uniform in thickness, by which not only the defects on the surface of the conductive substrate would not be covered effectively, but also the conductivity of the photoconductor would not be improved. For these reasons, it is unfavorable for the undercoat layer to have a thickness not falling within the above defined range.

In the electrophotographic photoconductor of the present invention, a photosensitive layer is provided on the undercoat layer. The photosensitive layer may have either a single-layer structure or a functionally distinguishable laminate structure. For high sensitivity and good durability, it is preferred that the photosensitive layer is of negatively chargeable type.

The electrophotographic photoconductor according to the present invention will be illustrated in more detail with reference to the drawings FIGS. 1 and 2 attached hereto.

Figure 1:
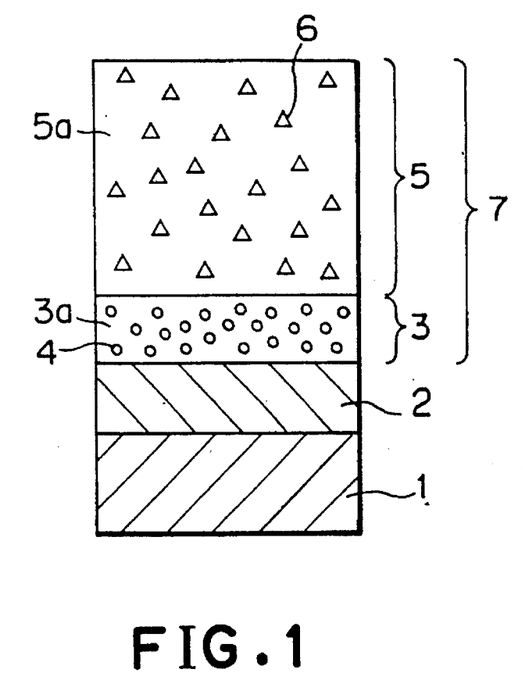
FIG. 1 is a cross-sectional view illustrating a main part of an embodiment of the electrophotographic photoconductor according to the present invention, in which the photosensitive layer has a functionally distinguishable laminate structure.

FIG. 1 is a cross-sectional view of a main part of the electrophotographic photoconductor according to the present invention, which comprises a photoconductor of a single-layer type.

Figure 2:
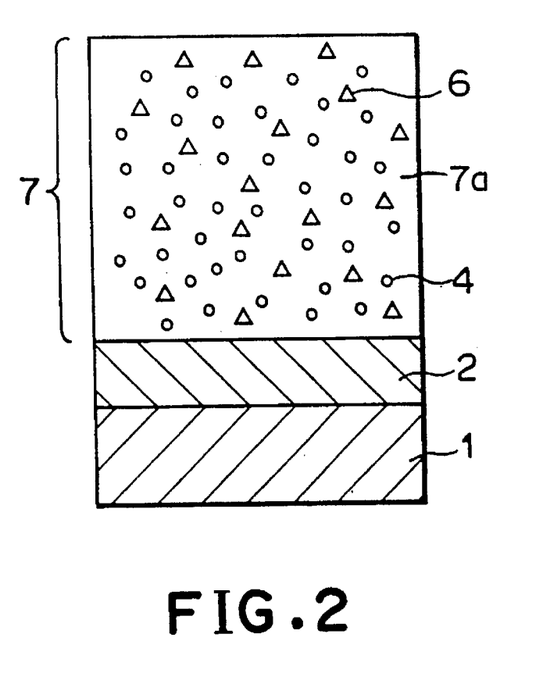
FIG. 2 is a cross-sectional view illustrating a main part of another embodiment of the electrophotographic photoconductor according to the present invention, in which the photosensitive layer has a single-layer structure.

FIG. 2 is a cross-sectional view of a main part of the electrophotographic photoconductor according to the present invention, which comprises a photoconductor of a functionally distinguishable laminate type.

In FIGS. 1 and 2, each of the reference numbers indicates as follows:

1: conductive substrate;
2: undercoat layer;
3: charge-generation layer;
3a: binder for charge-generation layer;
4: charge-generation substance;
5: charge-transport layer;
5a: binder for charge-transport layer;
6: charge-transport substance;
7: photosensitive layer; and
7a: binder for photosensitive layer.

In both of the photoconductors of FIGS. 1 and 2, the conductive substrate preferably used is a metallic substrate made of, for example, aluminum, stainless steel or nickel; and an insulating substrate such as a polyester film or a substrate made of paper or glass each of which having on its surface a conductive layer made of aluminum, copper, vanadium, tin oxide, indium oxide or the like. Among them, the most preferred substrate is an aluminum pipe.

On the conductive substrate 1, an undercoat layer 2 is provided by a known method. As mentioned above, the undercoat layer 2 according to the present invention comprises a polyamide resin and methylhydrogenpolysiloxane-treated titanium dioxide and preferably styrene-maleic acid half-ester copolymer. The undercoat layer can be formed, for example, in such a manner that these components are dispersed in a mixture solvent of an alcohol-type solvent and a halogenated hydrocarbon-type solvent to prepare a coating liquid for an undercoat layer; then the resultant coating liquid is applied onto a conductive substrate 1 and then dried to form an undercoat layer on the conductive substrate.

In the electrophotographic photoconductor of FIG. 1 (in which the photosensitive layer 7 is of a functionally distinguishable type), the photosensitive layer 7 comprises two layers, that is, a charge-generation layer 3 provided on the undercoat layer 2 and a charge-transport layer 5 provided on the charge-generation layer 3. The charge-generation layer 3 contains a charge-generation substance 4 dispersed in a binder 3a, and the charge-transport layer 5 contains charge-transport substances 6 dispersed in a binder 5a. Examples of the charge-generation substance 4 include inorganic photoconductive materials such as selenium and alloys thereof, cadmium sulfide, and the like; and organic pigments such as phthalocyanine pigments, azo pigments, bisazo pigments, trisazo pigments, squalilium pigments, pyrylium pigments, perylene pigments, anthanthrone pigments, and the like. These materials may be used alone or in combination with one or more of them. With respect to the binder 3a to be used in the charge-generation layer 3, there is not particular limitation as long as it has an electrical insulation property and enables to form a film. However, especially preferred are poly(vinyl ketals) such as poly(vinyl formal), poly(vinyl acetal) and poly(vinyl butyral), acrylic resins, styrene-based resins, polyester resins, polycarbonate resins, vinyl chloride-based resins, vinyl acetate-based resins, silicone resins, and the like. In the charge-generation layer 3, it is desirable to use the binder 3a in an amount of within the range of 10 to 300 wt % based on the weight of the charge-generation substance 4. The charge-generation layer 3 has a thickness of 0.01 to 2 μm.

On the charge-generation layer 3, is provided a charge-transport layer 5 which contains charge-transport substance 6. As for the charge-transport substance 6 and the binder 5a used, any of the conventional charge-transport substances and binders can be used. Examples of the charge-transport substance 6 include pyrazoline-type compounds, hydrazone-type compounds, styryl-type compounds, triphenylmethane-type compounds and triphenylamine-type compounds. Examples of the binder include polyester resins and polycarbonate resins. The charge-transport layer 5 of the present invention can be formed by first dissolving the charge-transport substance 6 and the binder 5a in an appropriate solvent to obtain a coating liquid, and then the resultant coating liquid is applied onto the charge-generation layer and dried to obtain a charge-transport layer 5 having a thickness of 5 to 50 μm. If desired, the charge-transport layer 5 may contain various additives such as antioxidants.

On the other hand, in the electrophotographic photoconductor of FIG. 2, the photosensitive layer 7 is of a single-layer type and comprises both a charge-generation substance 4 and a charge-transport substance 6 both of which are dispersed in a binder 7a. The charge-generation substance 4, the charge-transport substance 6 and the binder 7a may be those which can also be used for the electrophotographic photoconductor of FIG. 1. For the preparation of the photosensitive layer 7 of this type, these components are dissolved in a suitable solvent to obtain a coating liquid, and the resultant coating liquid is applied onto an undercoat layer 2 (which has been providing on a conductive substrate 1) and then dried; thus, providing a photosensitive layer 7 having a thickness of 10 to 50 μm. The photosensitive layer 7 of this type may also contain various additives such as antioxidant.

As mentioned above, the electrophotographic photoconductor according to the present invention is characterized by comprising an undercoat layer provided between a conductive substrate and a photosensitive layer, in which the undercoat layer comprises a polyamide resin and methylhydrogenpolysiloxane-treated titanium dioxide and preferably styrene-maleic acid half-ester copolymer as the undercoat layer components. Accordingly, the photoconductor of the present invention is hardly suffered from the decrease in charging property and sensitivity and the rise in residual potential under the repeated use. The photoconductor of the present invention is also hardly affected by the influence of environmental conditions, even high temperature/high humidity and low temperature/low humidity conditions.

Furthermore, in the present invention, since the undercoat layer components are dispersed in a mixture solvent of an alcohol-type solvent (e.g., methanol, ethanol, isopropyl alcohol, n-propyl alcohol, etc.) and a halogenated hydrocarbon-type solvent (e.g., methylene chloride, dichloroethane, trichloroethane, etc.) to prepare a coating liquid for the undercoat layer, the resultant coating liquid can be applied onto a conductive substance uniformly.

EXAMPLES

The present invention will be illustrated in more detail with reference to the following Examples, but should not be construed as limiting the scope of the invention.

Example 1

A photoconductor, in which the photosensitive layer had a functionally distinguishable multi-layer structure comprising a charge-generation layer and a charge-transport layer, was produced in the following manner.

That is, in a mixture solvent formed of 70 parts by weight of methyl alcohol and 30 parts by weight of dichloromethane, were added 3.15 parts by weight of nylon-12/6/66 copolymer ("Daiamid T-171"; a trade name by Daicel-Hüls), 0.8 part by weight of styrene-maleic acid half-ester copolymer ("AP-20"; a trade name by BASF) and 6.1 parts by weight of methylhydrogenpolysiloxane-treated titanium dioxide ("SI-UFTR-ZF"; a trade name by Miyoshi Kasei Inc.). The resultant mixture was dispersed for 10 hours by means of a ball mill, thereby obtaining a coating liquid for an undercoat layer which contained 10 wt % of the treated titanium dioxide. Into the coating liquid thus prepared, an aluminum cylinder (which having an outer diameter of 30 mm, a length of 245.3 mm, a thickness of 1 mm and a surface roughness of 0.8 S) was immersed, thereby providing an undercoat layer having a dry thickness of 0.5 μm on the cylinder.

On the other hand, 2.1 parts by weight of the azo compound having the following formula 1 and 10 parts by weight of poly(vinyl acetal) ("Slec KS-1"; a trade name by Sekisui Chemical Ind. Co.,) were dispersed in a mixture of 16 parts by weight of methyl ethyl ketone and 9 parts by weight of cyclohexanone by means of a sand mill, and then 75 parts by weight of methyl ethyl ketone was further added thereto to prepare a coating liquid for a charge-generation layer.

Formula 1:

This compound can be prepared according to the method, for example, described in U.S. Pat. No. 4,988,594.

Into the coating liquid, was immersed the aluminum cylinder with the undercoat layer prepared above, thereby providing a charge-generation layer on the undercoat layer having a dry thickness of 0.2 μm.

10 Parts by weight of hydrazone-based compound having the following formula 2 and 10 parts by weight of polycarbonate ("Upilone PCZ-300"; a trade name by Mitsubishi Gas Chemical Co., Ltd.) were dissolved in 80 parts by weight of tetrahydrofuran to provide a coating liquid for a charge-transport layer. The resultant coating liquid was then applied onto the charge-generation layer prepared above, thereby obtaining a charge-transport layer having a thickness of 20 μm on the charge-generation layer. Thus, a photoconductor was produced.

Formula 2:

This hydrazone compound can be produced by, for example, the method described in U.S. Pat. No. 4,957,837.

The photoconductor thus obtained was loaded in a commercially available copying machine ("Model Z-25"; manufactured by Sharp Corporation) for 50,000 copies making test run under three different environmental conditions, that is, a low temperature/low humidity condition (5° C., 20% relative humidity (RH)), a normal temperature/normal humidity condition (22° C., 50% RH) and a high temperature/high humidity condition (35° C., 80% RH).

The photoconductor thus prepared was evaluated on its various characteristics. The items and the methods therefor are as follows:

(1) Electric characteristics

The following electric characteristics were measured utilizing an electrostatic recording paper testing apparatus (Kawaguchi Denki Model EPA8100).

The initial dark potential (Vd) and the initial light potential (Vi) of the surface of the photoconductor had been adjusted to −600 V and −30 V, respectively. Then, the intensity of light irradiated was shifted so that the surface potential changed from −600 to −300, and the light amount required for this shift was defined as the half decay exposure amount (lx·s), which was an index of photosensitivity of the photoconductor. The residual potential (Vr) was defined as the potential of the photoconductor surface which was given when exposed at an exposure amount of 10 lx·s.

The photoconductor was subjected to 50,000-copies making test run, and then measured on the above items.

(2) Image quality

A solid black original paper and a solid white original paper were respectively copied using the copying machine equipped with the photoconductor. The image quality of each of the copied images from the solid black original and the solid white original was evaluated before and after the 50,000-copies making run. In the results in Table 1, the term "good' means that neither fogging on the copied image of the white original nor white fine spots on the copied image of the black original was observed; the term "white spots on a black paper" means that the copied image of the white original was good but the copied image of the black original had white fine spots thereon; the term "fog on a white paper" means that the copied image of the black original was good but the copied image of the white original showed fogging thereon; and the term "After 50.000 C" means "After 50,000-copies making run".

(3) Stability of coating liquid

Two photoconductor were produced using the coating liquid for the undercoat layer just after preparation and the coating liquid after the storage for 30 days. The appearance of the surface of each of the resultant photoconductors are examined visually.

(4) Adhesion property

This item was evaluated according to the grid test method prescribed in JIS K5400. That is, a cutter with thin blades was used to make cut lines so that the cut reached the substrate in an axis-wise direction and a rotation-wise direction at 1 mm intervals on the photoconductor; thus 1 mm×1 mm squares defined by the cut lines were formed, to thereby obtain cut patterns of the film composed of the photosensitive layer and the undercoat layer. Then, an adhesive tape with a width of 24 mm was pressed on the surface of the undercoat layer so that the adhered area becomes 24 mm×25 mm. Subsequently, the adhesive tape was pulled off in the rotation-wise direction and the number of the peeled squares of the film was counted.

In Table 1, the term "good" means that no square of the film was peeled off; and the term "poor" means that one or more squares of the film were peeled off.

Example 2

Substantially the same procedure as in Example 1 was repeated except that the polycyclic quinone compound of the following formula 3 was used as the charge-generation substance, thereby obtaining a photoconductor.

Formula 3:

The resultant photoconductor was evaluated on the various characteristics in the same manner as in Example 1.

Example 3

Substantially the same procedure as in Example 1 was repeated except that the azo compound of the following formula 4 was used as the charge-generation substance, thereby obtaining a photoconductor.

Formula 4:

The resultant photoconductor was evaluated on the various characteristics in the same manner as in Example 1.

Comparative Examples 1–3

Substantially the same procedure as in each of Examples 1 to 3 was repeated except that the undercoat layer did not contain the treated titanium dioxide and applied on the substrate in a thickness of 0.3 μm. Thus, three comparative photoconductors corresponding to the photoconductors of Examples 1 to 3, respectively, were obtained. The resultant photoconductors were evaluated on the various characteristics in the same manner as in Example 1.

Comparative Examples 4–6

Substantially the same procedure as in each of Examples 1 to 3 was repeated except that no undercoat layer was provided between the substrate and the charge-generation layer. Thus, three comparative photoconductors corresponding to the photoconductors of Examples 1 to 3, respectively, were obtained. The resultant photoconductors were evaluated on the various characteristics in the same manner as in Example 1.

Comparative Example 7

Substantially the same procedure as in Example 1 was repeated except that the solvent for dispersing the undercoat layer components was composed of methyl alcohol alone, thereby obtaining a comparative photoconductor. The resultant photoconductor was evaluated on the various characteristics in the same manner as in Example 1.

Comparative Example 8

Substantially the same procedure as in Example 1 was repeated except that the undercoat layer contained no styrene-maleic acid half-ester copolymer and was applied on the substrate in a thickness of 0.5 μm, thereby obtaining a comparative photoconductor. The resultant photoconductor was evaluated on the various characteristics in the same manner as in Example 1.

Comparative Example 9

Substantially the same procedure as in Example 1 was repeated except that the undercoat layer contained the untreated titanium dioxide (i.e., titanium dioxide not treated with methylhydrogenpolysiloxane) and was applied on the substrate in a thickness of 0.5 μm, thereby obtaining a comparative photoconductor. The resultant photoconductor was evaluated on the various characteristics in the same manner as in Example 1.

Comparative Example 10

Substantially the same procedure as in Example 1 was repeated except that the undercoat layer contained the titanium dioxide which had been subjected to a conductive plating treatment with gold and was applied on the substrate in a thickness of 0.5 μm, thereby obtaining a comparative photoconductor. The resultant photoconductor was evaluated on the various characteristics in the same manner as in Example 1.

The results of Examples 1 to 3 and Comparative Examples 1 to 10 are summarized in Table 1.

TABLE 1

| | | Dulability | | | | | Stability of coating liquid | | |
| --- | --- | --- | --- | --- | --- | --- | --- | --- | --- |
| | | Electric characteristics | | | | Image quality | | Appearance | |
| | Environmental conditions | Vd (V) | Vi (V) | Sensitivity (lx · s) | Vr (V) | Initial | After 50,000 C | Initial | After 30 days | Adhesive property |
| Example 1 | 5° C., 20% | −597 | −42 | 1.52 | −17 | good | good | good | good | good |
| | 22° C., 50% | −595 | −40 | 1.50 | −15 | good | good | | | |
| | 35° C., 85% | −592 | −39 | 1.50 | −14 | good | good | | | |
| Example 2 | 5° C., 20% | −596 | −37 | 1.51 | −15 | good | good | good | good | good |
| | 22° C., 50% | −595 | −35 | 1.50 | −14 | good | good | | | |
| | 35° C., 85% | −594 | −32 | 1.50 | −14 | good | good | | | |
| Example 3 | 5° C., 20% | −595 | −34 | 1.52 | −17 | good | good | good | good | good |
| | 22° C., 50% | −595 | −35 | 1.55 | −14 | good | good | | | |
| | 35° C., 85% | −594 | −34 | 1.54 | −12 | good | good | | | |
| Comparative Example 1 | 5° C., 20% | −575 | −150 | 2.1 | −70 | fog on a white paper | fog on a white paper | good | good | good |
| | 22° C., 50% | −570 | −140 | 2.0 | −50 | good | fog on a white paper | | | |
| | 35° C., 85% | −568 | −115 | 1.9 | −40 | good | fog on a white paper | | | |
| Comparative Example 2 | 5° C., 20% | −576 | −153 | 2.2 | −92 | fog on a white paper | fog on a white paper | good | good | good |
| | 22° C., 50% | −575 | −130 | 2.0 | −50 | good | fog on a white paper | | | |
| | 35° C., 85% | −569 | −124 | 1.8 | −46 | good | fog on a white paper | | | |
| Comparative Example 3 | 5° C., 20% | −567 | −180 | 2.4 | −105 | fog on a white paper | fog on a white paper | good | good | good |
| | 22° C., 50% | −560 | −130 | 2.2 | −60 | good | fog on a white paper | | | |
| | 35° C., 85% | −567 | −110 | 2.1 | −58 | good | fog on a white paper | | | |
| Comparative Example 4 | 5° C., 20% | −594 | −42 | 1.51 | −16 | white spots on a black paper | white spots on a black paper | good | good | good |
| | 22° C., 50% | −592 | −39 | 1.50 | −15 | white spots on a black paper | white spots on a black paper | | | |
| | 35° C., 85% | −584 | −36 | 1.50 | −13 | white spots on a black paper | white spots on a black paper | | | |
| Comparative Example 5 | 5° C., 20% | −596 | −40 | 1.52 | −18 | white spots on a black paper | white spots on a black paper | good | good | good |
| | 22° C., 50% | −593 | −33 | 1.52 | −15 | white spots on a black paper | white spots on a black paper | | | |
| | 35° C., 85% | −585 | −35 | 1.50 | −16 | white spots on a black paper | white spots on a black paper | | | |
| Comparative Example 6 | 5° C., 20% | −593 | −41 | 1.55 | −18 | white spots on a black paper | white spots on a black paper | good | good | good |
| | 22° C., 50% | −594 | −36 | 1.53 | −15 | white spots on a black paper | white spots on a black paper | | | |
| | 35° C., 85% | −587 | −34 | 1.53 | −13 | white spots on a black paper | white spots on a black paper | | | |
| Comparative Example 7 | 5° C., 20% | −595 | −39 | 1.52 | −17 | good | good | good | poor | good |
| | 22° C., 50% | −596 | −37 | 1.50 | −14 | good | good | | | |
| | 35° C., 85% | −593 | −34 | 1.50 | −14 | good | good | | | |
| Comparative Example 8 | 5° C., 20% | −593 | −40 | 1.57 | −19 | good | good | good | good | poor |
| | 22° C., 50% | −594 | −37 | 1.53 | −16 | good | good | | | |
| | 35° C., 85% | −591 | −34 | 1.54 | −15 | good | good | | | |
| Comparative Example 9 | 5° C., 20% | −592 | −41 | 1.52 | −17 | white spots on a black paper | white spots on a black paper | poor | poor | good |
| | 22° C., 50% | −593 | −38 | 1.50 | −16 | white spots on a black paper | white spots on a black paper | | | |
| | 35° C., 85% | −591 | −35 | 1.51 | −13 | white spots on a black paper | white spots on a black paper | | | |
| Comparative Example 10 | 5° C., 20% | −554 | −43 | 1.75 | −23 | white spots on a black | white spots on a black | poor | poor | good |

TABLE 1-continued

| | Dulability | | | | | | Stability of coating liquid | | |
|---|---|---|---|---|---|---|---|---|---|
| | Electric characteristics | | | | Image quality | | Appearance | | |
| Environmental conditions | Vd (V) | Vi (V) | Sensitivity (lx · s) | Vr (V) | Initial | After 50,000 C | Initial | After 30 days | Adhesive property |
| 22° C., 50% | −535 | −38 | 1.72 | −21 | paper white spots on a black paper | paper white spots on a black paper | | | |
| 35° C., 85% | −511 | −34 | 1.71 | −19 | paper white spots on a black paper | paper white spots on a black paper | | | |

As is apparent from the test results shown in Table 1, the photoconductors according to the present invention (Examples 1 to 3) exhibited less change in charging property, residual potential and sensitivity and showed a good image quality even after continuous production of 50,000 copies.

Example 4

A plate-type photoconductor in which the photosensitive layer had a single-layer structure was produced in the following manner.

That is, as a conductive substrate, an aluminum plate (30 mm×30 mm×1 mm) was used. On the substrate, was provided an undercoat layer prepared in the same manner as in Example 1 in a thickness of 0.5 µm.

Subsequently, 5 parts by weight of the amine compound of the following formula 5 as the charge-transport substance, 5 parts by weight of polycarbonate ("Upilon PCZ-300"; a trade name by Mitsubishi Gas Chemical Co., Ltd.) and 0.3 part by weight of butylated hydroxytoluene (BHT) were dissolved in 45 parts by weight of tetrahydrofurane to obtain a solution.

Formula 5:

Into the resultant solution, was added 0.5 part by weight of the azo compound of the following formula 6 as the charge-generation substance, thereby obtaining a coating liquid for a photosensitive layer. The resultant coating liquid was applied onto the undercoat layer by means of the wire bar technique. The resultant was dried at 110° C. for 60 minutes. Thus, a plate-type photoconductor having a photosensitive layer of 20 µm thick was produced.

Formula 6:

The photoconductor thus manufactured was subjected to a measurement of the half decay exposure amount (lx.s) (which was an index of photosensitivity) using an electrostatic recording paper testing apparatus (Kawaguchi Denki Model EPA8100). That is, an initial surface potential was measured when the surface of the photoconductor was positively charged in the dark by corona discharge at +6.0 kV for 10 seconds. After the surface potential of the photoconductor was measured in the dark, the surface of the photoconductor was irradiated with white light at an illuminance of 2 lx untie the charging potential decreased to half its initial value, in which the total amount of the irradiated light was determined as the half decay exposed amount (lx·s). Also, the surface potential of the photoconductor after 5 seconds of irradiation thereof with white light at an illuminance of 2 lx. was measured as a residual potential. With respect to the charging potential and the residual potential, the tests were carried out before and after the 5,000 copies making run.

The results are shown in Table 2 below.

Comparative Example 11

Substantially the same procedure was repeated except that the undercoat layer was not provided between the substrate and the photosensitive layer, thereby obtaining a comparative photoconductor. The resultant photoconductor was evaluated in the same manner as in Example 4. The results are also shown in Table 2.

Example 4 exhibited an excellent properties under repeated use compared with Comparative Example 11.

TABLE 2

|  | Half decay exposure amount (lx · s) | Characteristics under repeated use | | | |
| --- | --- | --- | --- | --- | --- |
|  |  | Charging potential (V) | | Residual potential (V) | |
|  |  | Initial | After 5,000C | Initial | After 5,000c |
| Ex. 4 | 3.3 | +551 | 531 | 87 | 91 |
| Comp. Ex. 11 | 3.4 | +548 | 322 | 89 | 90 |

As described above, the photoconductor according to the present invention, which comprising an undercoat layer provided between a conductive substrate and a photosensitive layer, is characterized in that the undercoat layer mainly comprises nylon-12/6/66 copolymer and methylhydrogenpolysiloxane-treated titanium dioxide and, preferably, styrene-maleic acid half ester copolymer. Consequently, the photoconductor can be prevented from suffering from the image defects, the decrease in charging property and the rise of residual potential under repeated use. The photoconductor of the present invention can also keep its stability over repeated use and under wide environmental conditions.

In addition, the photoconductor of the present invention is also characterized in that the undercoat layer is prepared by first dissolving the treated titanium dioxide and the nylon-12/6/66 copolymer and, preferably, styrene-maleic acid half ester copolymer in a mixture solvent of an alcohol-type solvent (such as methyl alcohol, ethyl alcohol, isopropyl alcohol and n-propyl alcohol) and a halogenated hydrocarbon-type solvent (such as methylene chloride, dichloroethane and trichloroethylene) to obtain a coating liquid for the undercoat layer, and then applying the dispersion liquid onto the conductive substrate. Consequently, the undercoat layer can be provided on the substrate uniformly, by which it becomes possible to produce an electrophotographic photoconductor having an excellent image quality.

The present invention has been described in detail with respect to preferred embodiments, and it will now be apparent from the foregoing to those skilled in the art that changes and modifications may be made without departing from the invention in its broader aspect, and it is the invention, therefore, in the apparent claims to cover all such changes and modifications as fall within the true spirit of the invention.

What is claimed is:

1. An electrophotographic photoconductor comprising:
   an conductive substrate;
   an undercoat layer provided on the conductive substrate; and
   a photosensitive layer having both charge-generation and charge-transport functions provided on the undercoat layer,
   wherein said undercoat layer comprises a polyamide resin and a methylhydrogenpolysiloxane-treated titanium dioxide.

2. The electrophotographic photoconductor as claimed in claim 1, wherein said undercoat layer further comprises styrene-maleic acid half-ester copolymer.

3. The electrophotographic photoconductor as claimed in claim 1, wherein said polyamide resin is nylon-12/6/66 copolymer.

4. The electrophotographic photoconductor as claimed in claim 1, wherein said undercoat layer has a thickness of within the range from 0.1 to 10 μm.

5. The electrophotographic photoconductor as claimed in claim 1, wherein said photosensitive layer has a functionally distinguishable laminate structure comprising a charge-generation layer having a charge-generation function and a charge-transport layer having a charge-transport function, in which the charge-generation layer and the charge-transport layer are laminated on the substrate in this order.

6. The electrophotographic photoconductor as claimed in claim 1, wherein said photosensitive layer has a single-layer structure.

7. A method for producing an electrophotographic photoconductor comprising the steps of:
   (1) dispersing a polyamide resin and methylhydrogenpolysiloxane-treated titanium dioxide in a mixture solvent formed of an alcohol-type solvent and a halogenated hydrocarbon-type solvent, thereby preparing a coating liquid for an undercoat layer;
   (2) applying said coating liquid onto a conductive substrate, thereby providing an undercoat layer on the substrate; and
   (3) forming a photosensitive layer on said undercoat layer.

8. The method as claimed in claim 7, wherein, in said step (1), styrene-maleic acid half-ester copolymer is further dispersed together with said polyamide resin and methylhydrogenpolysiloxane-treated titanium dioxide into said mixture solvent.

9. The method as claimed in claim 7, wherein said step (3) comprises the following steps of:
   (a) forming a charge-generation layer on said undercoat layer; and
   (b) forming a charge-transpiring layer on said charge-generation layer.

10. The method as claimed in claim 7, wherein said polyamide resin is nylon-12/6/66 copolymer.

* * * * *